(12) United States Patent
Woolston

(10) Patent No.: US 8,387,809 B2
(45) Date of Patent: Mar. 5, 2013

(54) MEDICAMENT CARTRIDGE ASSEMBLY

(75) Inventor: Robert Woolston, Warwick (GB)

(73) Assignee: DCA Design International Limited, Warwick (GB)

( * ) Notice: Subject to any disclaimer, the term of this patent is extended or adjusted under 35 U.S.C. 154(b) by 319 days.

(21) Appl. No.: 12/461,951

(22) Filed: Aug. 28, 2009

(65) Prior Publication Data

US 2010/0004617 A1    Jan. 7, 2010

Related U.S. Application Data

(63) Continuation of application No. 11/438,275, filed on May 23, 2006, which is a continuation of application No. 10/308,148, filed on Dec. 3, 2002, now abandoned.

(30) Foreign Application Priority Data

Dec. 6, 2001    (GB) .................................. 0129176.4

(51) Int. Cl.
*B65D 51/00*    (2006.01)
*A61M 5/32*    (2006.01)
(52) U.S. Cl. .................. 215/247; 215/DIG. 3; 215/230; 604/415
(58) Field of Classification Search .................. 215/317, 215/247, 249, 230, DIG. 3; 604/415, 411
See application file for complete search history.

(56) References Cited

U.S. PATENT DOCUMENTS

| | | | |
|---|---|---|---|
| 3,916,893 A | 11/1975 | De Felice | |
| 3,977,555 A | 8/1976 | Larson | |
| 4,018,640 A | 4/1977 | Amberg | |
| 4,402,417 A | 9/1983 | Corrigan, Jr. et al. | |
| 5,085,332 A | 2/1992 | Gettig et al. | |
| 5,137,528 A | 8/1992 | Crose | |
| 5,230,707 A * | 7/1993 | Laderoute | 604/86 |
| 5,303,835 A | 4/1994 | Haber et al. | |
| 5,334,162 A | 8/1994 | Harris | |
| 5,360,410 A | 11/1994 | Wacks | |
| 5,454,409 A | 10/1995 | McAffer et al. | |
| 5,549,561 A | 8/1996 | Hjertman | |
| 5,641,010 A | 6/1997 | Maier | |
| 5,693,027 A | 12/1997 | Hansen et al. | |
| 5,709,668 A | 1/1998 | Wacks | |

(Continued)

FOREIGN PATENT DOCUMENTS

| | | |
|---|---|---|
| EP | 0 063 891 | 11/1982 |
| EP | 0 550 767 | 7/1993 |

(Continued)

*Primary Examiner* — Anthony Stashick
*Assistant Examiner* — James N Smalley
(74) *Attorney, Agent, or Firm* — Oliff & Berridge, PLC

(57) ABSTRACT

A person having diabetes will often be required to take both slow acting and fast acting forms of insulin. It is important to be able to distinguish readily between medicament cartridges containing different medicaments. The present invention enables more ready distinction as between medicament cartridges containing different medicaments. An adaptor top for a medicament cartridge, the medicament cartridge comprising a cylinder having a main body portion, a neck portion at a first end having a radially outwardly directed flange portion, a narrowing shoulder portion connecting the body portion and the neck portion, a cap beaded across the first end thereby to retain a fluid impermeable membrane, and the adaptor top comprising a first cylindrical body portion having a radially inwardly directed flange at one end, in use to be seated over and against the cap and a second cylindrical skirt portion being adapted, in use, to be seated against the shoulder portion of the cartridge, the second skirt portion including a plurality of fingers, the free ends of the fingers in use being adapted to be seated beneath the outwardly directed flange of the medicament cartridge.

2 Claims, 1 Drawing Sheet

U.S. PATENT DOCUMENTS

| | | |
|---|---|---|
| 5,957,314 A | 9/1999 | Nisida et al. |
| 5,971,181 A | 10/1999 | Niedospial, Jr. et al. |
| 6,227,371 B1 | 5/2001 | Song |
| 6,328,174 B1 | 12/2001 | Marangoni et al. |
| 6,379,340 B1 | 4/2002 | Zinger et al. |
| 6,745,505 B2 | 6/2004 | Moran |
| 6,904,867 B2 | 6/2005 | Zamjahn |

FOREIGN PATENT DOCUMENTS

| | | |
|---|---|---|
| EP | 0 829 248 | 3/1998 |
| EP | 0 937 473 | 8/1999 |
| EP | 0 990 446 | 4/2000 |
| EP | 1 094 012 | 4/2001 |
| GB | 2 190 303 | 12/1987 |
| WO | WO 80/00828 | 5/1980 |
| WO | WO 89/07462 | 8/1989 |
| WO | WO 93/02720 | 2/1993 |
| WO | WO 2005049443 A1 * | 6/2005 |

* cited by examiner

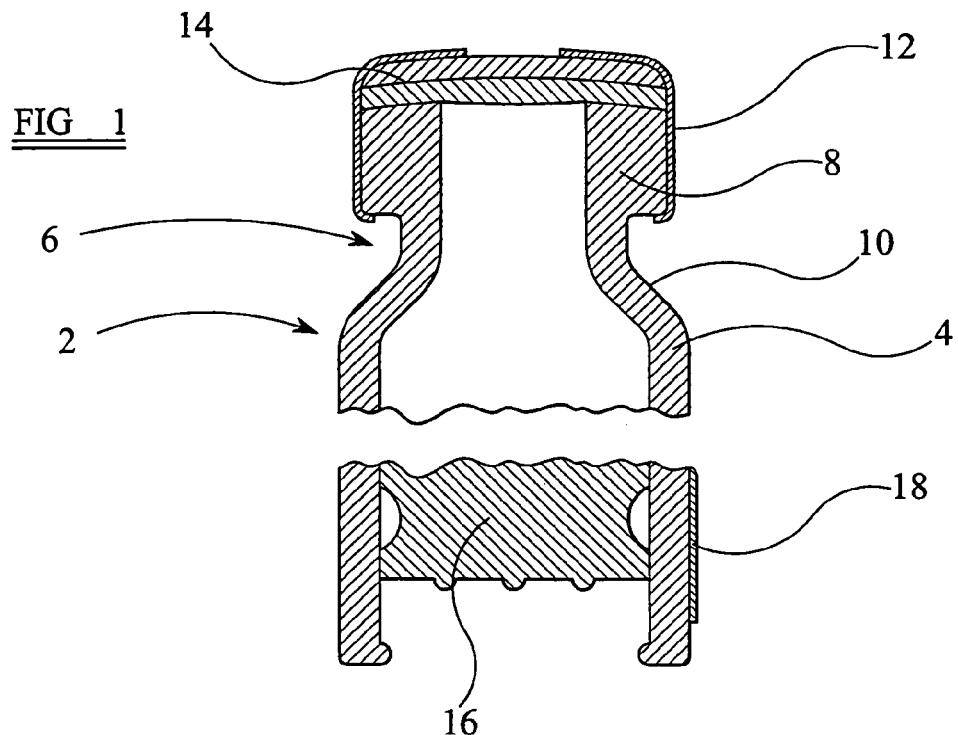
FIG 1
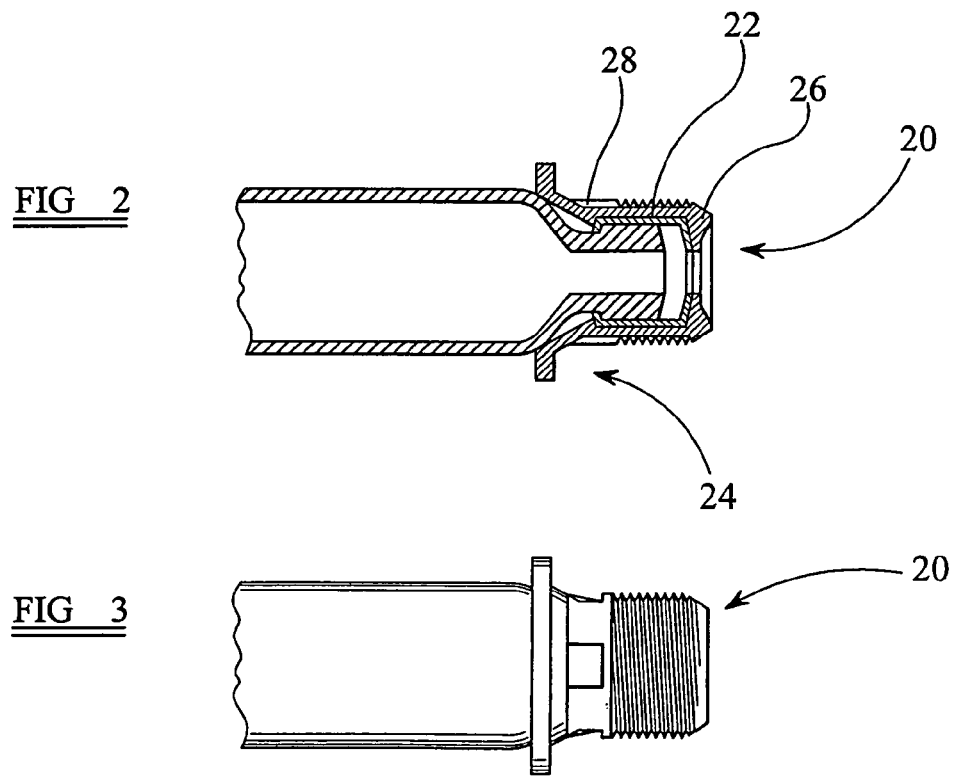
FIG 2
FIG 3

MEDICAMENT CARTRIDGE ASSEMBLY

This is a Continuation of application Ser. No. 11/438,275 filed May 23, 2006, which is a Continuation of application Ser. No. 10/308,148 filed Dec. 3, 2002. The disclosure of these prior applications are hereby incorporated by reference herein in their entirety.

FIELD OF THE INVENTION

The present invention relates to a improved medicament cartridge assembly and, in particular, but not exclusively, to a medicament cartridge assembly for use with a medication delivery apparatus such as an injection pen or an infuser.

Such medication delivery apparatus are conveniently used to provide a means for administration of a medicament to a patient without medical supervision, for example, by self administration or administration by a carer.

BACKGROUND TO THE INVENTION

Medicament cartridges are produced in large volumes to take advantage of economies of scale. The medicament cartridges will then be filled with an appropriate medicament, such as insulin or a human growth hormone.

However, it is often the case that a patient will require more than one form of medicament. A person having diabetes will often be required to take both slow acting and fast acting forms of insulin. It is important that a user of the medicament delivery apparatus is able to distinguish readily between medicament cartridges containing different medicaments.

It is an advantage of the present invention that it enables the user to distinguish readily between medicament cartridges containing different medicaments. It is a further advantage that the present invention makes use of known medicament cartridges, thereby enabling economies of scale to be maintained.

SUMMARY OF THE INVENTION

According to the first aspect of the present invention there is provided an adaptor top for a medicament cartridge, the medicament cartridge comprising a cylinder having a main body portion, a neck portion at a first end having a radially outwardly directed flange portion, a narrowing shoulder portion connecting the body portion and the neck portion, a cap beaded across the first end thereby to retain a fluid impermeable membrane, the adaptor top comprising a first cylindrical body portion having a radially inwardly directed flange at one end, in use to be seated over and against the cap and a second cylindrical skirt portion being adapted, in use, to be seated against the shoulder portion of the cartridge, the second skirt portion including a plurality of fingers, the free ends of the fingers in use being adapted to be seated beneath the outwardly directed flange of the medicament cartridge.

According to a second aspect of the present invention, a method of assembling a medicament cartridge and an adaptor top, the medicament cartridge comprising a cylinder having a bottleneck at a first end, a fluid impermeable membrane secured across the first end by a cap and a displaceable plunger located internally of the cylinder towards the second end of the cylinder, and the adaptor top comprising a first cylindrical portion having at a first end an inwardly directing flange and a second cylindrical portion depending from a second end of the first cylindrical portion, the second cylindrical skirt portion including a number of deformable members, comprising the steps of inserting the cap of the medicament cartridge through the second cylindrical portion into the first cylindrical portion until the cap is positioned against the inwardly directed flange;

plastically deforming the deformable members beneath the cap to retain the adaptor top in position against the medicament cartridge.

The adaptor top may conveniently be provided with information regarding the content of the medicament cartridge. Preferably, the adaptor top is colour coded to provide information regarding the content of the medicament cartridge.

BRIEF DESCRIPTION OF THE DRAWINGS

The present invention will now be described, by way of example only, with reference to the accompanying drawings, in which:

FIG. 1 shows a part-cut-away section through a known medicament cartridge,

FIG. 2 shows a section through a medicament cartridge assembly in accordance with the present invention, and FIG. 3 shows a side view of the assembly of FIG. 2.

DETAILED DESCRIPTION OF THE INVENTION

Referring to FIG. 1 there may be seen a known cartridge for use with the present invention. The medicament cartridge 2 comprises a cylinder 4 having a main body portion. A neck portion 6 is provided at first end of the body portion. The neck portion 6 includes a radially outwardly directed flange portion 8. A narrowing shoulder portion 10 connects the body portion and the neck portion 6. A cap 12 is provided beaded across the first end of the cylinder 4 thereby to retain a fluid impermeable membrane 14 across an open end of the neck portion 6.

A piston 16 is provided within the cylinder 4. In use, a needle unit (not shown) pierces the fluid impermeable membrane 14 such that movement of the piston 16 towards the first end of the body portion causes the contents of the medicament cartridge to be expelled through the needle unit. The cylinder 4 may additionally be provided with a label 18 providing information about the medicament cartridge 2 and the contents of the medicament cartridge 2.

Referring now to FIGS. 2 and 3 an adaptor top 20 for a medicament cartridge is shown. The adaptor top 20 comprises a first cylindrical body portion 22 and a second skirt portion 24. The first cylindrical body portion 22 has a radially inwardly directed flange 26 at one end. In use the radially inwardly directed flange is seated over and against the cap 12 and the second skirt portion 24 is seated against the shoulder portion 10 of the cartridge 2.

The first cylindrical body portion 22 is conveniently formed with engagement means. In the embodiment of FIG. 3 the engagement means takes the form of a screw thread 23 formed integrally with the first cylindrical body portion 22. In use, the engagement means enables an assembly comprising the medicament cartridge 2 and adaptor top 20 to be received and secured within a medicament delivery apparatus such as an infusion or injection device from which the contents of the medicament cartridge 2 may be dispensed.

The second skirt portion 24 includes a plurality of deformable members or fingers 28. The fingers 28 are formed at a first end integrally with the adaptor top 20. The fingers 28 are plastically deformable.

In order to assemble the adaptor top 20 with the medicament cartridge 2, the cap 12 of the medicament cartridge 2 is inserted through the second skirt portion 24 into the first cylindrical portion 22 until the cap 12 is in contact with the inwardly directed flange 26. The fingers 28 are then plastically deformed such that free ends of the fingers 28 are located beneath the cap 12 thereby to retain the adaptor top 20 in position in relation to the medicament cartridge 2. Since the free ends of the fingers 28 are now located beneath the cap 12 between the cap 12 and the shoulder portion 10 of the cartridge 2, it is difficult for a user or other third party to remove the adaptor top 20 from the medicament cartridge 2 without damaging the fingers 28. In this way, the adaptor top 20 and the associated medicament cartridge 2 provide a tamper evident assembly.

What is claimed is:

1. A method of assembling a medicament cartridge and an adaptor top, the medicament cartridge comprising a cylinder having a bottleneck at a first end, a fluid impermeable membrane secured across the first end by a cap and a displaceable plunger located internally of the cylinder towards a second end of the cylinder, and the adaptor top comprising a first cylindrical portion having at a first end an inwardly directing flange and a second cylindrical portion depending from a second end of the first cylindrical portion, and a second cylindrical skirt portion including a number of deformable members with free ends and being seated against a narrowing shoulder portion of the medicament cartridge, comprising the steps of:

inserting the cap of the medicament cartridge through the second cylindrical portion into the first cylindrical portion until the cap is positioned against the inwardly directed flange; and plastically deforming the free ends beneath the cap to retain the adaptor top in position against the medicament cartridge.

2. The method according to claim 1, in which the adaptor top is color coded to provide information regarding the content of the medicament cartridge.

* * * * *